United States Patent [19]

Zwahlen

[11] 4,264,500

[45] Apr. 28, 1981

[54] PROCESS OF MAKING 6-CHLORO-α-METHYL-CARBAZOLE-2-ACETIC ACID

[75] Inventor: Willy Zwahlen, Thürnen, Switzerland

[73] Assignee: Hoffmann-La Roche Inc., Nutley, N.J.

[21] Appl. No.: 125,529

[22] Filed: Feb. 28, 1980

[30] Foreign Application Priority Data

Mar. 2, 1979 [CH] Switzerland ............... 2104/79

[51] Int. Cl.³ .................................... C07D 209/82
[52] U.S. Cl. .................................... 260/315
[58] Field of Search ........................ 260/315

[56] References Cited

U.S. PATENT DOCUMENTS

| 3,896,145 | 7/1975 | Berger et al. | 260/315 |
| 4,158,007 | 6/1979 | Gurien et al. | 260/315 |

OTHER PUBLICATIONS

Ashmore et al., *Synthetic Communications*, vol. 6, (1976), pp. 399–402.
Acheson et al., *J. Chem. Soc., Perkin*, (1972), pp. 1569–1576.
Ebel, *Helv. Chim. Acta.*, vol. 12, (1929), pp. 2–19.
Bruck, *Chemical Communications*, (1970), p. 1690.
Borsche, *Annalen*, vol. 359, (1907), pp. 49–80.
Grinev et al., *Chem. Abstracts*, vol. 80, (1974), No. 82540q.
Grinev et al., *Khimiko–Farmatsevticheskii Zhurnal*, vol. 7, (1973), pp. 19–21.
Derwent 40716, (3-5-1968), Dutch Pat. Publication 69 06059.
Derwent G8859, (25-5-1965), U.S. 3,317,552.
Derwent 62340T, (5-2-1971), Japanese Pat. Publication 4,717,760.
Derwent 33801W, (17-11-1972), Russian Patent 437,770.

*Primary Examiner*—Henry R. Jiles
*Assistant Examiner*—R. W. Ramsuer
*Attorney, Agent, or Firm*—Jon S. Saxe; Bernard S. Leon; William G. Isgro

[57] ABSTRACT

The aromatization of (6-chloro-1,2,3,4-tetrahydro-2-carbazolyl)-methyl-malonic acid dialkyl ester, utilizing chlorine and subsequent conversion of the resulting product to 6-chloro-α-methyl-carbazole-2-acetic acid by hydrolysis and decarboxylation are described.

5 Claims, No Drawings

PROCESS OF MAKING 6-CHLORO-α-METHYL-CARBAZOLE-2-ACETIC ACID

BRIEF SUMMARY OF THE INVENTION

The invention relates to the aromatization of a compound of the formula

[Structure I: 6-chloro-tetrahydrocarbazole with CH₃ and C(COOR)₂ substituent]

wherein
R is lower alkyl,
by treatment with chlorine and subsequent hydrolysis and decarboxylation of the resulting compound of the formula

[Structure II: 6-chloro-carbazole with CH₃ and C(COOR)₂ substituent]

wherein
R is as previously described,
to yield 6-chloro-α-methyl-carbazole-2-acetic acid.

DETAILED DESCRIPTION OF THE INVENTION

The invention relates to a process for the preparation of 6-chloro-α-methyl-carbazole-2-acetic acid, which is known for its pharmaceutical properties.

6-Chloro-α-methyl-carbazole-2-acetic acid has been prepared by treating 6-chloro-α-methyl-1,2,3,4-tetrahydrocarbazole-2-acetic acid ethyl ester with an aromatizing agent, such as, p-chloranil and subsequently hydrolyzing the resulting 6-chloro-α-methyl- carbazole-2-acetic acid ethyl ester. A disadvantage of this known process is the use of aromatizing agents such as p-chloranil which lead to the formation of undesired by-products, especially of chlorine-containing by-products which are difficult to use. Another disadvantage of this process comprises the fact that the aromatizing agent cannot be removed directly and can be regenerated only in an expensive manner.

In accordance with the invention, there is provided a process by which 6-chloro-α-methyl-carbazole-2-acetic acid can be prepared in high yield and without the aforementioned disadvantages. The process provided by the present invention comprises aromatizing a compound of the formula

[Structure I]

wherein
R is lower alkyl,
by treatment with chlorine and hydrolyzing and decarboxylating the resulting compound of the formula

[Structure II]

wherein
R is as previously described.

The lower alkyl group denoted by R in formulas I and II hereinbefore can be branched-chain or, preferably, straight-chain. Examples of such lower alkyl groups are methyl, ethyl, propyl, isopropyl, butyl, and the like; methyl and especially ethyl are preferred.

The aromatization of a compound of formula I is conveniently carried out in an aprotic solvent such as toluene, methylene chloride or ethylene chloride, preferably toluene, at an elevated temperature, especially up to the reflux temperature of the mixture, while slowly adding chlorine. Preferably, chlorine is added within about 2 to 8 hours, preferably over a period of about 4 hours. When methylene chloride is used as the solvent the aromatizaton is conveniently carried out at about 40° C. and when toluene is used as the solvent the aromatization is conveniently carried out at a temperature in the range of from about 50° C. to the reflux temperature of the mixture, preferably at about 75° C.

The compounds of formula II can be isolated from the mixture in a known manner, for example, by crystallization, or can be subjected in situ to the subsequent step of the process.

The hydrolysis and decarboxylation of a compound of formula II can be carried out simultaneously in a known manner by treatment with acids, for example, by means of glacial acetic acid in the presence of a hydrohalic acid, such as, hydrochloric acid.

The process provided by the present invention can be carried out batchwise or, preferably, continuously.

The starting materials of formula I can be obtained by reacting an α-methyl-3-oxocyclohexane-malonic acid di(lower alkyl) ester of the formula

[Structure III: 3-oxocyclohexane with CH₃ and C(COOR)₂ substituent]

wherein
R is as previously described,
with p-chlorophenylhydrazine, conveniently in an inert organic solvent, for example, an alkanol, such as, ethanol, at a temperature in the range of from about 25° C. to 100° C., preferably at room temperature.

The Examples which follow further illustrate the invention. All temperatures are stated in degrees Centigrade, unless otherwise mentioned.

EXAMPLE I

Preparation of 6-chloro-α-methyl-carbazole-2-acetic acid 2.5 Kg. of (6-chloro-1,2,3,4-tetrahydro-2-carbazolyl)-methyl-malonic acid diethyl ester are introduced into a 100 liter reaction vessel and 75 liters of toluene are added. The mixture is heated to 75° C. with stirring and the vessel is evacuated to −0.6 bar. 940 G. of chlorine gas are passed in slowly within 4 hours.

The solution is cooled to 20° C. 10 Liters of deionized water are added. The pH of the aqueous phase is adjusted to 8–9 with 1.25 kg. of sodium bicarbonate and the aqueous phase is separated. 10 Liters of deionized water are added to the toluene phase, the mixture is stirred and the aqueous phase is separated. The combined aqueous phases are extracted with 15 liters of methylene chloride. The methylene chloride phase is evaporated in vacuo, the toluene phase is added and the mixture is concentrated to a volume of 5 liters in vacuo. It is then cooled to 0° C. and stirred at this temperature overnight. The product is removed by filtration under suction and washed with 1 liter of toluene. After drying overnight in vacuo at 60° C., there are obtained 2.1 kg. (85% of theory) of (6-chloro-2-carbazolyl)-methyl-malonic acid diethyl ester having a melting point of 134°–136° C.

The mother liquors from several batches are concentrated to 1/10 of their volume. After crystallization, there are obtained an additional 170 g. (6.8%) of product per batch.

A mixture of 247 g. of (6-chloro-2-carbazolyl)-methyl-malonic acid diethyl ester, 1.9 liters of glacial acetic acid and 1.9 liters of 6 N hydrochloric acid is heated under reflux overnight with stirring and the resulting black solution is cooled to room temperature. The solid formed is removed by filtration, washed with acetic acid/water (1:1) and water and then dried. The 192 g. of crude 6-chloro-α-methyl-carbazole-2-acetic acid obtained are dissolved in 1.2 liters of 1 N potassium hydroxide, the solution is extracted with four 300 ml. portions of diethyl ether and acidified by the addition of 100 ml. of concentrated hydrochloric acid while cooling in an ice-bath under nitrogen. The mixture is stirred for 15 minutes, the precipitated solid is removed by filtration, washed with water and dried. 167.7 G. of product are obtained. The last purification is carried out by crystallization from 4.7 liters of boiling 1,2-dichloroethane with 8.0 g. of active carbon. The solution is cooled overnight, the crystals are removed by filtration, washed with dichloroethane and dried. There are obtained 103.8 g. (57.3% of theory) of almost white 6-chloro-α-methyl-carbazole-2-acetic acid having a melting point of 198.5°–201° C.

The (6-chloro-1,2,3,4-tetrahydro-2-carbazolyl)-methyl-malonic acid diethyl ester used as the starting material can be prepared as follows:

2.5 G. of sodium are added to 325 ml. of ethanol, the solution is treated within 5 minutes with 200 g. of methyl-malonic acid diethyl ester and the mixture is stirred for 1 hour. A solution of 100 g. of 2-cyclohexan-1-one in 130 ml. of ethanol is then added within a one hour period. The resulting mixture is stirred overnight. After the addition of 20 ml. of acetic acid, the mixture is evaporated, the resulting oil is dissolved in 1.31 liters of diethyl ether and the solution is washed with water. The ethereal solution is dried, filtered and again dried. Thereafter, the ether is removed under reduced pressure and the residual oil is distilled in vacuo. There are obtained 211.5 g (75.4% of theory) of α-methyl-3-oxocyclohexane-malonic acid diethyl ester having a boiling point of 129°–130° C./0.2.

A mixture of 100 g. of α-methyl-3-oxocyclohexane-malonic acid diethyl ester, 66.3 g. of p-chlorophenyl-hydrazine hydrochloride and 300 ml. of ethanol is stirred for 1.5 hours and then heated under reflux for 1.5 hours. The mixture is left to stand at room temperature overnight. Then, it is cooled in an ice-bath and the crystals are removed by filtration. The filter cake is dried, washed with ice-cold ethanol and then with hexane/ethanol (1:1) and dried. The 91.7 g. of solid obtained are stirred with 50 ml. of water in an ice-bath under nitrogen, filtered, washed with water and dried. There are obtained 78.8 g. (56.5% of theory) of (6-chloro-1,2,3,4-tetrahydro-2-carbazolyl)-methyl-malonic acid diethyl ester having a melting point of 129°–130° C.

I claim:

1. A process for preparing 6-chloro-α-methyl-carbazole-2-acetic acid, which comprises aromatizing a compound of the formula

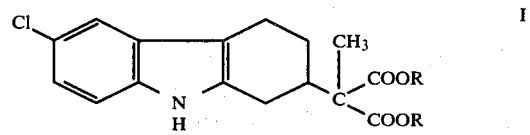

wherein
R is lower alkyl,
by treatment with chlorine, and therafter hydrolyzing and decarboxylating the resulting compound of the formula

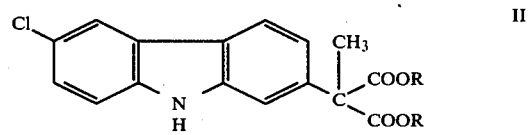

wherein
R is as previously described.

2. A process in accordance with claim 1, wherein a compound of formula I wherein R is ethyl is utilized.

3. A process in accordance with claim 1, wherein a compound of formula I where R is methyl is utilized.

4. A process in accordance with claims 1, 2 or 3, wherein the aromatization is carried out in an aprotic solvent.

5. A process in accordance with claims 1, 2 or 3, wherein the aprotic solvent is toluene.

* * * * *